United States Patent [19]
Webster et al.

[11] Patent Number: 6,162,646
[45] Date of Patent: Dec. 19, 2000

[54] URINE PH INDICATOR SYSTEM AND ASSOCIATED METHODS

[75] Inventors: William H. Webster, 714 Commercial St., Portland, Me. 04101; Alfred E. Fox, Newton, Mass.

[73] Assignee: William H. Webster, Portland, Me.

[21] Appl. No.: 09/080,857

[22] Filed: May 18, 1998

Related U.S. Application Data

[63] Continuation of application No. 08/831,519, Apr. 1, 1997, abandoned.
[60] Provisional application No. 60/014,671, Apr. 3, 1996.
[51] Int. Cl.⁷ .......................... G01N 21/80; G01N 21/78; G01N 21/77
[52] U.S. Cl. ............................ 436/166; 436/163; 422/56
[58] Field of Search .................................. 436/163, 166; 422/55, 56, 57; 119/171, 172, 173

[56] References Cited

U.S. PATENT DOCUMENTS

| | | |
|---|---|---|
| 4,770,878 | 9/1988 | Thomas . |
| 5,143,023 | 9/1992 | Kuhns . |
| 5,267,532 | 12/1993 | Franklin et al. ........................ 119/173 |
| 5,409,472 | 4/1995 | Rawlings et al. . |
| 5,415,131 | 5/1995 | Dodman .................................. 119/171 |
| 5,468,450 | 11/1995 | Michael . |
| 5,578,317 | 11/1996 | Mulder . |

*Primary Examiner*—Alexander Markoff
*Attorney, Agent, or Firm*—Selitto & Associates

[57] ABSTRACT

A urine pH indicator has a plurality of hydrophilic, non-ionic, polymer foam carrier particles. The carrier particles are impregnated with an indicator complex having more than one chromophore and indicating more than one pH threshold via at least three distinguishable colors. The carrier particles are preferable chopped and soaked in a solution containing the chromophore complex. Upon evaporation of the solvent, the chromophore complex is bound to the carrier particles which can then be spread upon animal litter to receive urine and indicate pH via color display.

10 Claims, No Drawings

URINE PH INDICATOR SYSTEM AND ASSOCIATED METHODS

CROSS REFERENCE TO RELATED APPLICATIONS

This is a continuation application of U.S. application Ser. No. 08/831,519 filed Apr. 1, 1997, now abandoned, which is a §111(a) application relating to U.S. application Ser. No. 60/014,671 filed Apr. 3, 1996.

FIELD OF THE INVENTION

The present invention relates to pH indicators and methods and, more particularly, to indicators and methods for indicating that the pH of feline urine is in a normal or abnormal range, either in the acidic or alkaline direction.

BACKGROUND OF THE INVENTION

It is known that urine pH can be interpreted to provide information concerning the physiological state of an animal. For instance, the urine of a healthy cat has a pH ranging from about 6.4 to about 6.8. Many feline diseases are accompanied by a shift in urinary pH from the normal pH range to an acidic or alkaline condition. Abnormal urine pH may indicate viral-infections, cystitis, secondary infections from procedures, such as spaying or hysterectomies, complications from feline leukemia and other pathologies. Many of the common causes of abnormal feline urinary pH are referred to cumulatively as Feline Lower Urinary Tract Disease (FLUTD) or feline urological syndrome (FUS).

Besides being symptomatic of a variety of diseases, abnormal Urinary pH has its own associated pathology, such as, the formation of uroliths or crystals associated with FLUTD. A pH reading above 7 may give rise to the growth of magnesium ammonium phosphate crystals, or struvites, while a pH below 6.4 is conducive to the formation of calcium oxalate crystals. Each of these conditions is uncomfortable and unhealthy for the effected animal. It would therefore be desirable for cat owners to be alerted to abnormal urine pH as soon as possible such that they can seek early diagnosis and treatment of their cat's potential health problems by a qualified veterinarian, thus sparing the cat from pain, illness and/or death. A product and method for monitoring urinary pH would also be valuable as part of a program for cats who are recuperating from or have been treated for disease.

U.S. Pat. No. 5,143,023 describes a litter for the accumulation of animal urine having a visual indicator chemically bound to the litter base material. The litter is used to ascertain the pH of an animal's urine to indicate potential pathology. The patent teaches that the litter base material must have the ability to exchange ions in order to bind the pH indicating molecules to the litter base material while leaving the pH-sensitive reactive groups available to indicate the presence of ions. U.S. Pat. No. 5,143,023 also proposes neutralizing the litter base material, e.g., clay, to prevent the indicator from interacting with the base material upon which it is directly deposited. U.S. Pat. No. 5,143,023 suggests that more than one indicator can be used, but advises that consumer-directed litters be limited to two indicators. The examples provided in U.S. Pat. No. 5,143,023 test for one pH threshold and exhibit one color change.

Another known animal urine pH testing kit utilizes strips of paper treated with a chemical reagent. To perform a test, the strips are placed on top of or in the cat litter in a litter box. When the cat urinates on the strips, the strips exhibit a color change. Because the strips are physically distinct from the cat litter, they interfere with the cat's normal use of the litter box such that the cat may avoid urinating on the test strips in the litter box. The strips are preferably removed from the litter box after the test and compared to a graduated color scale. The necessity of retrieving the used litmus paper from the litter box and holding a color scale in proximity to it is inconvenient and unpleasant. Perhaps more importantly, the testing of urine pH by introducing litmus paper to a litter box is subject to false pH readings due to the pH effect of the litter on the urine solution contacting the litmus paper. Furthermore, litmus paper typically exhibits only one color change to indicate a shift of pH across a single pH threshold. It is therefore an object of the present invention to provide a pH indicator material that is accurate and compatible with cat litter such that a cat does not avoid the indicator, is easy to use and is calibrated to provide pronounced color indicia associated with acidic, normal and alkaline urine pH.

SUMMARY OF THE INVENTION

The present invention overcomes the disadvantages and shortcomings of prior art urine pH indicators by providing an indicator material and method for making and using it. The indicator material has a plurality of hydrophilic carrier particles impregnated with a pH indicator. The indicator material is capable of displaying more than one color state in response to the pH of a solution to which the indicator material is exposed.

DETAILED DESCRIPTION OF THE EXEMPLARY EMBODIMENT

A pH indicator material in accordance with the present invention includes a multitude of small absorbent, low-density, carrier particles, each impregnated and/or coated with a pH indicator system or complex of pH sensitive chromophores. As noted above, the various materials used for producing cat litter, e.g., kaolin, attapulgite, montmorillonite, zeolite, bentonite and sepiolite clays and vermiculite, have their own pH effect in solution. In testing animal urine, it is likely that the pH of a urine sample would be changed if combined with cat litter of the foregoing common types, thus giving inaccurate readings. The present invention avoids the foregoing test contamination attributable to the litter by utilizing a separate, pH neutral, hydrophilic substrate impregnated with a pH indicating complex. The substrate is comminuted or formed into a multiplicity of particles that compete with the litter material in absorbing urine. Urine directly absorbed into the particles of the present invention does not interact with the litter material and therefore will provide an accurate pH indication when it reacts with the indicator complex on the carrier particles. In this manner, urine pH is tested and indicated independently of the cat litter.

Because the present pH indicating material is independent of the litter material, i.e., indicators are not coated on the litter, it is not effected by litter pH properties and can be used with all known types of litters. The carrier particles of the present invention are preferably hydrophilic foam made by the process of emulsifying a polyurethane prepolymer and an aqueous phase in a mixer so as to thoroughly mix the two phases, essentially instantaneously. The emulsion is deposited between a sandwich of release paper or suitable material, into a mold, or otherwise placed so it will produce the desired physical form.

After placement, the emulsion goes through the well known chemical and physical processes associated with polymer foams, viz., "blowing", "creaming", "gelation", becoming "tack-free", etc. During this process, the emulsion solidifies and through the release of carbon dioxide, expands to create a typical foam structure. A suitable prepolymer may be obtained commercially from a number of manufacturers. For instance, Hampshire Chemical produces appropriate prepolymers under the trade name Hypol™. Rynel, Ltd. produces another workable family of prepolymers under the Trepol trade name. Other manufacturers produce similar products acceptable for this invention.

The prepolymers are the reaction product of a difunctional isocyanate (e.g., Toluene Diisocyanate) and a polyfunctional glycol (e.g., polyethylene glycol). The reaction mixture might also contain other components to catalyze or otherwise produce crosslinking. The aqueous phase contains certain components which facilitate the emulsion with the prepolymer and also affect the surface of the resultant foam. Typically a nonionic surfactant is used. The Pluronic family produced by BASF may be used, but other surfactants known in the art, such as silicone-based surfactants may be used as well. The concentration of these surfactants is between 0.001% and 2% by weight.

As mentioned, the surfactant aids in the emulsification. It also has the effect of "opening up" the cells of the foam. This is necessary so as to take full advantage of the hydrophilic surface area of the foam. The surfactant can also control the surface energy of the foam, thus making it "fast wicking" or "slow". Wicking is the speed at which a fluid is absorbed into the foam. The resultant foam according to the present invention is said to be "open celled". It is nonionic and has low extractables.

Example 1(A)

50 grams of Trepol (Rynel Ltd., Boothbay, Me.) is mixed with 100 grams of an aqueous solution of 0.05 % Pluronic L-62. The emulsion is poured into a wax-lined cup and allowed to react for 20 minutes. It is then removed from the cup and fully saturated with water by immersion. The saturated foam is put into a Waring type blender, where it is chopped until it appears to be liquified. The chopped foam is removed from the blender, squeezed to remove excess water and packaged for subsequent imbibing with the indicator complex solution.

Because the carrier particles of the present invention compete for a limited amount of urine with the cat litter, the carrier particles are preferably sized, shaped and surfaced to maximize the absorption of urine. While surface area would be increased by finer and finer comminution, other considerations suggest that extremely fine particles are not desirable. Namely, the particles must be large enough for the pH indication to be seen by the user when the particles are applied to/mixed with the cat litter. The particles must also be large enough to avoid being inadvertently inhaled, ingested or tracked out of the litter box by a cat. Furthermore, the indicator material preferably has a lower density than the cat litter. This permits the indicator material to remain close to or "float" to the surface of the litter, e.g., when pawed by a cat, where it can compete most favorably with the litter to absorb urine. If the indicator material particle size is not comparable to that of the litter, it will, despite lower density, fall through the pores/spaces between the litter particles.

Carrier particles in accordance with the present invention can be formed/molded/cut into any particular aesthetically pleasing or interesting shape, e.g., toroidal, star-shaped, letters, animals, etc. all as known to one of normal skill in the plastic foam field. It is preferable to cut rather than mold the foam particles, however, in that the open-celled, cut surfaces of chopped particles absorb the indicator complex and urine better than a partially-sealed, molded surface. The above-described method of wet chopping the foam in a blender can be utilized to yield suitable, random-shape particles of approximately ⅛" to ¼" diameter. The carrier particles are porous for enhancing the liquid-absorbing capability of the indicator material, whereby cat urine can be readily absorbed into the carrier particles upon contact. In addition, the carrier particles are preferably more hydrophilic than the cat litter such that more urine is absorbed into the indicator than into the competing cat litter.

The other basic component of the present invention is the dye system that is combined with the carrier particles to yield a pH indicating material. The carrier particles are simply combined with the chromophore complex in solution, e.g., dissolved in an alcohol. The carrier particles absorb the indicator complex into their open cell structure which, upon evaporation of the solvent, becomes coated with the indicator complex.

The dye system of the present invention is a complex of pH sensitive chromophores (color producing indicators). Most pH sensitive dyes (indicators) exhibit a color shift over a relatively wide pH range. For example, Bromocresol purple changes from yellow to violet between the pH's of 5.2 and 6.8 and Alizarin turns from yellow to red between pH's of 5.6 and 7.1. When indicators are combined, however, in accordance with the present invention, a different response to pH is observed. Instead of indicating a broad pH range, the mixed indicator system can now determine pH between 5.2 and 6.0, and between 6.5 and 7.2, i.e., the indicator complex is more selective (indicates over a narrower range) and also indicates two distinct thresholds. This sensitivity is not possible with a single pH indicator.

By adding a third indicator one can prepare a system that is even more sensitive. After combining more than 3 dyes, however, the color response to pH becomes less, dramatic and most indicator systems fail upon adding more indicators. This is due to the overlap of the visible light absorption spectra for each dye which results in an overall flat response (resulting in a gray color).

The dye system of the present invention is a four to six component system including two to four chromophores, a humectant and a solvent. It is capable of distinguishing between pH 6.0 and 6.4 and pH 6.8 and 7.2 with the pH 6.0 to 6.4 transition resulting in a color change, e.g., from a yellow to green. The pH 6.8 to 7.2 transition results in a second color change, e.g., from green to blue.

Typical pH indicators that are suitable for this application consist of Bromocresol Purple. Bromothymol Blue, Neutral Red, Congo Red, Thymol Blue as well as a host of others. These indicators are readily available from Spectrum Chemical Mfg. Corp., New Brunswick, N.J.

The dye system is modified with suitable humectants in order to retain the color for as long as possible.

A typical system consists of a mixture of the above indicators as follows:

Example #1B

| | |
|---|---|
| Bromocresol Purple | 0.010 parts |
| Thymol Blue | 0.006 parts |

-continued

|  |  |  |
|---|---|---|
| Neutral Red | 0.003 | parts |
| Glycerin | 15.000 | parts |
| Ethanol | 85.000 | parts |
| Example #2 |  |  |
| Bromocresol Purple | 0.01 | parts |
| Thymol Blue | 0.01 | parts |
| Propylene Glycol | 9.98 | parts |
| Ethanol | 90.00 | parts |
| Example #3 |  |  |
| Bromothymol Blue | 0.020 | parts |
| Congo Red | 0.001 | parts |
| Thymol Blue | 0.005 | parts |
| Polyethylene Glycol | 12.000 | parts |
| (4 mole ethoxylate) |  |  |
| Ethanol | 88.000 | parts |
| Example #4 |  |  |
| Bromocresol Purple | 0.010 | parts |
| Bromothymol Blue | 0.010 | parts |
| Neutral Red | 0.003 | parts |
| Thymol Blue | 0.005 | parts |
| Glycerin | 10.000 | parts |
| Ethanol | 90.000 | parts |

The indicator material of the present invention as set forth in Example 1 above, exhibits an identifiable and distinguishable color prior to the first use of the indicator (i.e., before the indicator comes in contact with cat urine), viz., brownish orange. When wet with urine in the normal pH range, the indicator material assumes a greenish tint. The indicator material exhibits two different readily distinguishable colors corresponding respectively to acidic, and alkaline urine pH. Namely, when contacted by urine with a pH below 6.4, the indicator material turns yellow. Urine with pH from 6.4 to 6.8 causes the particle to display green, as noted above. At pHs above 68, the indicator material is blue. Accordingly, the indicator system of the present invention has been formulated such that each color is readily discernable by the user and displays a color for unused indicator, normal, acidic and alkaline urine.

The foregoing indicator system is chemically stable such that it does not break down or interact to spontaneously change color. In addition, the humectant in the dye system, e.g., glycerin retains the aqueous urine solution to preserve the color indicator for an extended period. As a result, it is not necessary to examine the indicator immediately after a cat's use of the litter box in order to monitor the pH of the cat's urine. The foregoing dye systems, alone and when deposited on the above-described carrier particles, are non-toxic to cats, as well as to humans. In addition, the carrier particles and the dye are bound together (with the indicator system adsorbed onto the surface and into the interior of the carrier particles) such that the dye is inhibited from staining a cat's paws and therefore indirectly staining household articles, such as furniture and carpeting. As noted, the carrier particles do not react with the dye system and/or the cat's urine to change the urine pH or its color indication. This is due to the fact that the carrier particle composition, e.g., polyurethane is not ionic and hence pH neutral. The indicator material therefore retains its color until it reacts with urine or the like and accurately reflects the pH of the wetting solution. As noted, the absorbency of the carrier particles inhibits the indicator from contacting and reacting with the litter. While polyurethane is the preferred composition for the carrier particles, any other absorbent, low density, non-toxic, non-ionic material could be employed.

In order to indicate the pH of cat urine, the indicator material, i.e., indicator coated foam, is preferably sprinkled on the surface of fresh cat litter. When the indicator material comes in contact with cat urine, the urine is absorbed into the carrier particles and comes in contact with the indicator complex, causing the color of the indicator to reflect urine pH. More particularly, if the urine has a pH within the normal range, the indicator exhibits its normal pH color; if the urine pH is above normal, the indicator exhibits its alkaline color and its acidic color if the urine has a pH below normal. A relatively alkaline or acidic condition in the urine can be caused by various transitory conditions (e.g., diet, stress or change in schedule). Accordingly, if an acidic or alkaline color is displayed, it should be noted. Persistent abnormal pH readings over the course of several days indicate that professional evaluation is appropriate. As a result, a veterinarian can be contacted for medical evaluation and treatment. In this regard, the present invention would be properly characterized as a pH indicator material rather than a diagnostic tool. Conclusions as to the presence of disease must be left to a qualified veterinary practitioner using proper diagnostic procedures and methods and cannot be drawn simply from the color display of a pH indicator.

It should be appreciated that the present invention provides advantages over the prior art discussed above, viz., it indicates acidic, normal and alkaline urine pH via easily discernable and interpretable color states. The indicator material accurately reflects the pH of a cat's urine by avoiding contamination of the test solution by cat litter which is, in itself, pH active. The indicator material is convenient to use by simply sprinkling it on the surface of the cat litter in a cat's litter pan. The tester need only view the indicator material after the cat urinates on it and observe the resultant color of the indicator material in order to ascertain if the cat's urine is acidic, alkaline or normal. The fluid retentive attributes of the indicator preserve col or display for extended periods, such that pH indication may be observed for a time after the animal's wetting on the material. Because the indicator material is non-toxic, non-staining, odorless and non-offensive to a cat, it can be left in the cat litter box after use and/or mixed with cat litter and does not interfere with the cat's normal use of the litter pan. The indicator material can be used to periodically or continuously monitor the pH of the urine of a healthy cat, as well as to monitor a cat recovering from urological disease.

It should be noted that the present invention can have many modifications, variations and applications. For instance, the indicator material can be premixed with cat litter sold to consumers or packaged as a separate additive. The indicator complex can be reconfigured to indicate other pH ranges, so as to be useful in connection with monitoring other diseases and conditions other than those discussed above. The indicator material of the present invention can also be used to monitor the urine pH of other animals, such as birds, cows, horses, zoo animals and other domestic, farm and/or caged animals. It should therefore be understood that the embodiments described herein are merely exemplary and that a person skilled in the art may make many variations and modifications therein without departing from the spirit and scope of the invention. All such variations and modifications are intended to be included within the scope of the present invention.

What is claimed is:

1. A pH indicator material, comprising:
   (a) a plurality of hydrophilic carrier particles;
   (b) a pH indicator impregnated on said carrier particles and displaying more than one color state in response to the pH of a solution to which said material is exposed, said pH indicator being a mixture of two or more chromophores, said mixture indicating at least two pH thresholds via a display of at least three different colors associated with corresponding pH ranges, said pH ranges having thresholds of 6.4 and 6.8 and wherein said colors are yellow, green and blue, respectively, for pH's below 6.4, between 6.4 and 6.8, and above 6.8.

2. The material of claim 1, wherein said carrier particles are non-ionic so as not to effect said more than one color state in response to said solution.

3. The material of claim 1, wherein said carrier particles are polymer foam.

4. The material of claim 1, wherein said carrier particles are polyurethane foam.

5. The material of claim 4, further including a humectant and wherein said chromophores are selected from the group: Bromocresol Purple, Thymol Blue, Neutral Red, Bromothymol Blue and Congo Red.

6. The material of claim 1, wherein said carrier particles are absorbent.

7. The material of claim 1, prepared by applying a mixture of a solvent with said mixture of chromophores to said hydrophilic carrier particles and evaporating said solvent.

8. The material of claim 5, wherein said humectant is Glycerin.

9. The material of claim 1, further including a humectant.

10. The material of claim 9, prepared by applying a mixture of a solvent with said mixture of chromophores and said humectant to said hydrophilic carrier particles and evaporating said solvent.

\* \* \* \* \*

UNITED STATES PATENT AND TRADEMARK OFFICE
CERTIFICATE OF CORRECTION

PATENT NO.    : 6,162,646  
DATED         : December 19, 2000  
INVENTOR(S)   : Webster et al.

Page 1 of 1

It is certified that error appears in the above-identified patent and that said Letters Patent is hereby corrected as shown below:

<u>Column 5,</u>
Line 36, change "68" to read -- 6.8 --.

Signed and Sealed this

Fifteenth Day of June, 2004

JON W. DUDAS  
*Acting Director of the United States Patent and Trademark Office*